US009322779B2

(12) United States Patent
Respini

(10) Patent No.: US 9,322,779 B2
(45) Date of Patent: Apr. 26, 2016

(54) METHODS OF MEASURING THE FOULING TENDENCY OF HYDROCARBON FLUIDS

(71) Applicant: Baker Hughes Incorporated, Houston, TX (US)

(72) Inventor: Marco Respini, Casalmorano (IT)

(73) Assignee: BAKER HUGHES INCORPORATED, Houston, TX (US)

( * ) Notice: Subject to any disclaimer, the term of this patent is extended or adjusted under 35 U.S.C. 154(b) by 69 days.

(21) Appl. No.: 14/055,425

(22) Filed: Oct. 16, 2013

(65) Prior Publication Data

US 2015/0102224 A1 Apr. 16, 2015

(51) Int. Cl.
*G01N 21/59* (2006.01)
*G01N 21/27* (2006.01)
*G01N 15/02* (2006.01)
*G01N 15/06* (2006.01)
*G01N 33/28* (2006.01)
*G01N 1/40* (2006.01)
*G01N 15/00* (2006.01)

(52) U.S. Cl.
CPC ............ *G01N 21/59* (2013.01); *G01N 15/0205* (2013.01); *G01N 15/06* (2013.01); *G01N 21/274* (2013.01); *G01N 33/2823* (2013.01); *G01N 2001/4083* (2013.01); *G01N 2015/0092* (2013.01); *G01N 2015/0693* (2013.01); *G01N 2201/06113* (2013.01)

(58) Field of Classification Search
CPC ... G01J 3/42; G01N 2030/8854; G01N 33/20; G01N 33/28; G01N 21/359; G01N 21/35; G01N 21/3577; G01N 17/008

USPC .................. 250/341.1, 301, 304, 343, 357.1, 250/339.12; 73/61.48, 341.1, 301, 304, 73/343, 357.1, 339.12, 61, 48
See application file for complete search history.

(56) References Cited

U.S. PATENT DOCUMENTS 2,854,396 A * 9/1958 Meinert et al. ................ 208/426
2,918,579 A * 12/1959 Dunlap et al. ................ 250/255
(Continued)

FOREIGN PATENT DOCUMENTS

WO 2011141826 A1 11/2011

OTHER PUBLICATIONS

Falkler, T., et al., "Fine-Tune Processing Heavy Crudes in Your Facility," Hydrocarbon Processing, pp. 67-73 (Sep. 2010).

*Primary Examiner* — David Porta
*Assistant Examiner* — Blake Riddick
(74) *Attorney, Agent, or Firm* — Mossman Kumar & Tyler PC

(57) ABSTRACT

A stability of at least one foulant within a hydrocarbon-based fluid sample may be determined where the hydrocarbon-based fluid sample may have or include, but is not limited to a hydrocarbon fluid and foulant particles. The fluid sample may have a viscosity ranging from about 0.5 cSt to about 5000 cSt. The hydrocarbon-based fluid sample may be centrifuged, and a laser light (in the near-infrared region) with a detector may be applied to the hydrocarbon-based fluid sample. At least one transmittance measurement from the laser light passing through the hydrocarbon-based fluid sample may be used to measure foulant flocculation. A foulant stability reserve measurement may be obtained by comparing a first transmittance measurement of the centrifuged hydrocarbon-fluid sample to a second transmittance measurement of a non-centrifuged hydrocarbon-fluid sample.

17 Claims, 4 Drawing Sheets

(56) References Cited

U.S. PATENT DOCUMENTS

| | | | |
|---|---|---|---|
| 3,496,350 A * | 2/1970 | Bray | 250/254 |
| 3,668,111 A * | 6/1972 | Dvoracek et al. | 208/48 AA |
| 3,795,810 A * | 3/1974 | Conley et al. | 250/343 |
| 4,021,335 A * | 5/1977 | Beaton | 208/309 |
| 4,390,412 A * | 6/1983 | Dvoracek et al. | 208/48 AA |
| 5,420,040 A | 5/1995 | Anfindsen et al. | |
| 6,839,137 B2 | 1/2005 | Mason et al. | |
| 6,841,779 B1 * | 1/2005 | Roehner et al. | 250/339.07 |
| 8,388,839 B1 * | 3/2013 | Hobson et al. | 210/232 |
| 2004/0040464 A1 * | 3/2004 | Andrievsky et al. | 106/31.49 |
| 2007/0284108 A1 * | 12/2007 | Roes et al. | 166/302 |
| 2008/0185316 A1 * | 8/2008 | Respini et al. | 208/48 Q |
| 2011/0278460 A1 * | 11/2011 | Respini | 250/340 |
| 2013/0009048 A1 * | 1/2013 | Xie et al. | 250/256 |
| 2013/0037719 A1 * | 2/2013 | Melling et al. | 250/340 |
| 2014/0326886 A1 | 11/2014 | Jennings et al. | |

* cited by examiner

METHODS OF MEASURING THE FOULING TENDENCY OF HYDROCARBON FLUIDS

TECHNICAL FIELD

The present invention relates to determining a stability of at least one foulant within a hydrocarbon-based fluid sample, and more specifically relates to centrifuging a hydrocarbon-based fluid sample and applying a laser light thereto for measuring the transmittance of the laser light through the hydrocarbon-based fluid sample at the time of foulant flocculation.

BACKGROUND

Various types of foulants pose problems during production and refining of hydrocarbon fluids. Foulants are materials within the production fluid that may become destabilized and agglomerate to each other and deposit on equipment, which can cause problems with the fluid during extraction, transporting, processing, refining, combustion, and the like. Examples of foulants include asphaltenes, iron sulfides, waxes, coke, sand, ores, clays, hydrates, naphthenates and the like.

Asphaltenes are most commonly defined as that portion of petroleum, which is soluble in xylene and toluene, but insoluble in heptane or pentane. Asphaltenes exist in crude oil as both soluble species and in the form of colloidal dispersions stabilized by other components in the crude oil. Asphaltenes have higher molecular weights and are the more polar fractions of crude oil, and can precipitate upon pressure, temperature, and compositional changes in crude oil resulting from blending or other mechanical or physicochemical processing. Asphaltene precipitation and deposition can cause problems in subterranean reservoirs, upstream production facilities, mid-stream transportation facilities, refineries, and fuel blending operations. In petroleum production facilities, asphaltene precipitation and deposition can occur in near wellbore reservoir regions, wells, flowlines, separators, and other equipment. Once deposited, asphaltenes present numerous problems for crude oil producers. For example, asphaltene deposits can plug downhole tubulars, wellbores, choke off pipes and interfere with the functioning of safety shut-off valves, and separator equipment. Asphaltenes have caused problems in refinery processes such as desalters, distillation preheat units, and cokers.

Many formation fluids, such as petroleum fluids, contain a large number of components with very complex compositions. For the purposes herein, a formation fluid is the product from a crude oil well from the time it is produced until it is refined. Some of the potentially fouling-causing components present in a formation fluid, for example asphaltenes, are stable in the crude oil under equilibrium reservoir conditions, but may aggregate or deposit as temperatures, pressures, and overall fluid compositions change as the crude oil is removed from the reservoir during production. Waxes comprise predominantly high molecular weight paraffinic hydrocarbons, i.e. alkanes. Asphaltenes are typically dark brown to black-colored amorphous solids with complex structures and relatively high molecular weights.

In addition to carbon and hydrogen in the composition, asphaltenes also may contain nitrogen, oxygen and sulfur species, and may also contain metal species such as nickel, vanadium, and iron. Typical asphaltenes are known to have different solubilities in the formation fluid itself or in certain solvents like carbon disulfide or aromatic solvents, such as benzene, toluene, xylene, and the like. However, the asphaltenes are insoluble in solvents like paraffinic compounds, including but not limited to pentane, heptane, octane, etc. Asphaltene stability can even be disturbed by mixing hydrocarbon-based fluids i.e. such as mixing two types of crude oils together, two types of shale oils together, condensates, and others, of different origins at certain ratios as the chemistry of the hydrocarbon-based fluids from different sources may be incompatible and induce destabilization of the asphaltenes therein. In non-limiting examples, such as during refining or fuel blending, two or more hydrocarbon-based fluids may be mixed together. Sometimes, changes in physical conditions are sufficient to induce destabilization, or even the mixture of different hydrocarbon-based fluids that have incompatible chemistries. Said differently, even if neither hydrocarbon-based fluid, alone, has destabilized foulants or the hydrocarbon-based fluid would not act as a destabilizing additive by itself, the mixing or the mixture of two or more hydrocarbon-based fluids may further destabilize the foulants present in either hydrocarbon-based fluid.

When the formation fluid from a subsurface formation comes into contact with a pipe, a valve, or other production equipment of a wellbore, or when there is a decrease in temperature, pressure, or change of other conditions, foulants may precipitate or separate out of a well stream or the formation fluid, while flowing into and through the wellbore to the wellhead. While any foulants separation or precipitation is undesirable in and by itself, it is much worse to allow the foulant precipitants to accumulate and deposit on equipment in the wellbore. Any foulant precipitants depositing on wellbore surfaces may narrow pipes and clog wellbore perforations, various flow valves, and other wellsite and downhole locations. This may result in wellsite equipment failures and/or closure of a well. It may also slow down, reduce or even totally prevent the flow of formation fluid into the wellbore and/or out of the wellhead.

Similarly, undetected precipitations and accumulations of foulants in a pipeline for transferring crude oil could result in loss of crude oil flow and/or equipment failure. Crude oil storage facilities could have maintenance or capacity problems if foulant precipitations occur. These fluids also carry unstable foulants into the refinery, as well as possibly into finished fuels and products where the foulants cause similar problems for facilities of this nature.

Accordingly, there are large incentives to mitigate fouling during refining. There are large costs associated with shutting down production units because of the fouling components within, as well as the cost to clean the units. The foulants may create an insulating effect within the production unit, reduce the efficiency and/or reactivity, and the like. In either case, reducing the amount of fouling would reduce the cost to produce hydrocarbon fluids and the products derived therefrom.

One technique to reduce the adverse effects of foulants within the formation fluid is to add a foulant inhibitor to the hydrocarbon-based fluid having potential fouling causing components. A 'foulant inhibitor' is defined herein to mean an inhibitor that targets a specific foulant. Several foulant inhibitors may be added to reduce the adverse effects of each type of foulant, e.g. asphaltene foulant inhibitors, iron sulfide foulant inhibitors, etc.; all may be added to the fluid to decrease the adverse effects of each type of foulant, such as deposition, accumulation, and/or agglomeration of the foulant(s). However, it has been difficult to analyze the stability or efficacy of the foulant inhibitors because the experimental conditions may not always represent actual 'field' conditions of the formation fluid.

There are several shortcomings when measuring foulant stability and/or efficacy of a foulant inhibitor to improve foulant stability. Thus, it would be desirable to develop better methods of analyzing the stability of the foulants and/or foulant inhibitors.

SUMMARY

There is provided, in one form, a method for determining a stability of at least one foulant within a hydrocarbon-based fluid sample having foulant particles. The hydrocarbon-based fluid sample may have a viscosity ranging from about 0.5 cSt independently to about 5000 cSt. The hydrocarbon-based fluid sample may be centrifuged, and then a laser light may be applied to the hydrocarbon-based fluid sample. The laser light may have a wavelength in the near-infrared region. A first transmittance of the laser light through the hydrocarbon-based fluid sample may be measured with a detector. A foulant stability reserve measurement may be obtained by comparing the first transmittance measurement of the centrifuged hydrocarbon-fluid sample to a second transmittance measurement of a non-centrifuged hydrocarbon-fluid sample.

In an alternative non-limiting embodiment of the method, the foulant particles may be present in the hydrocarbon fluid sample in an amount ranging from about 0.01 vol % to about 10 vol %. The method may include adding at least one solvent to the hydrocarbon-based fluid sample at about the same time as the centrifuging, before the centrifuging, after the centrifuging, and combinations thereof. A foulant stability reserve measurement may be obtained by comparing at least one transmittance measurement to the effective amount of the solvent added to the hydrocarbon-based fluid sample. After obtaining the foulant stability reserve measurement, the number or size of flocculated foulant particles may be analyzed by a technique, such as but not limited to, light scattering, light blocking, ultrasound, videomicroscopy, and combinations thereof.

In another non-limiting embodiment, the hydrocarbon-based fluid sample may be centrifuged for at least 30 seconds. The foulant particles present within the hydrocarbon-based fluid sample may be or include, but is not limited to asphaltenes, iron sulfides, waxes, coke, sand, ores, clays, hydrates, naphthenates, and combinations thereof.

Centrifuging the hydrocarbon-based fluid sample prior to measuring the transmittance and/or analyzing the number or size of foulant particles allows for foulant stability reserve measurements that are closer to field conditions of the hydrocarbon fluid.

DETAILED DESCRIPTION

Figure 1:
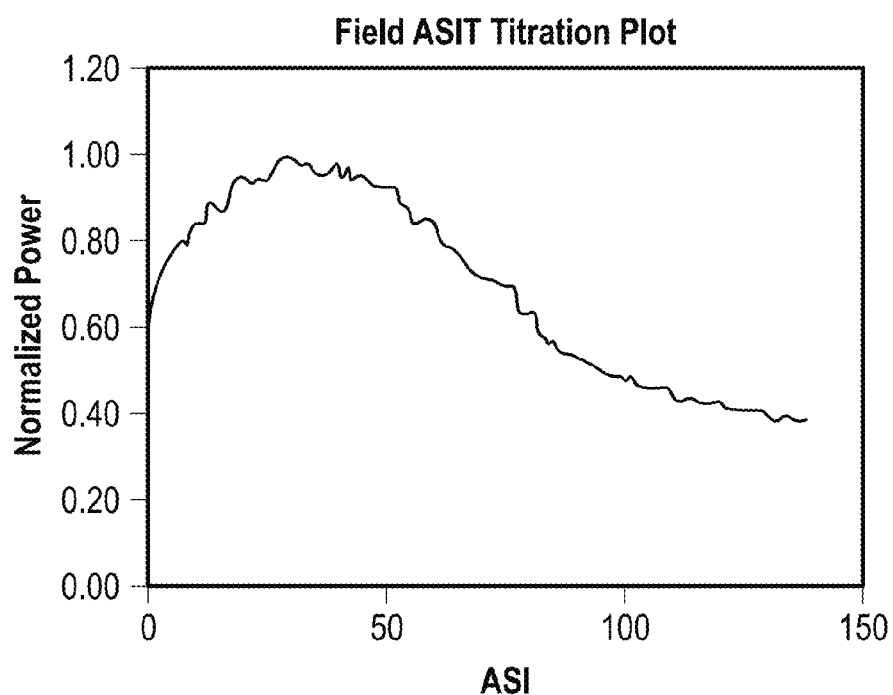
FIG. 1 is a graph illustrating the stability of a hydrocarbon-based fluid sample prior to centrifuging the hydrocarbon-based fluid sample.

It has been discovered that the stability of at least one foulant within a hydrocarbon-based fluid sample having a viscosity in a particular range may be measured. The hydrocarbon-based fluid sample may be centrifuged, and then a laser light with a detector may be applied to the hydrocarbon-based fluid sample. At least one transmittance measurement of the laser light through the hydrocarbon-based fluid sample may be measured. A foulant stability reserve measurement may be obtained by comparing a first transmittance measurement of the centrifuged hydrocarbon-fluid sample to a second transmittance measurement of a non-centrifuged hydrocarbon-fluid sample. "First transmittance" and "second transmittance" are only intended to distinguish the transmittance measurement for a centrifuged sample (i.e. a first transmittance measurement) and a non-centrifuged sample (i.e. a second transmittance measurement; either type of measurement may occur in time before or after the other. Moreover, more than one transmittance measurement may be taken for a centrifuged sample and/or a non-centrifuged sample.

The amount of time necessary to centrifuge the hydrocarbon-based fluid sample will vary depending on the type of hydrocarbon fluid, the type of foulants present, and the concentration of each within the sample. However, to give a general idea of the centrifuge times, the hydrocarbon-based fluid sample may be centrifuged for at least 30 seconds. In another non-limiting embodiment, the hydrocarbon-based fluid sample may be centrifuged for an amount of time ranging from about 1 minute independently to about 30 minutes, or from about 5 minutes independently to about 10 minutes in another non-limiting embodiment.

The amount of centrifugal force necessary when centrifuging the hydrocarbon-based fluid sample will vary depending on the type of hydrocarbon fluid, the type of foulants present, and the concentration of each within the sample. However, to give a general idea of the centrifugal force, the hydrocarbon-based fluid sample may be centrifuged at about 50 rpm independently to about 25000 rpm. In another non-limiting embodiment, the hydrocarbon-based fluid sample may be centrifuged at a centrifugal force ranging from about 200 rpm independently to about 5000 rpm, or from about 500 radius per minute independently to about 2000 radius per minute in another non-limiting embodiment.

The viscosity may range from about 0.5 cSt independently to about 5000 cSt. Alternatively, the viscosity may range from about 10 cSt independently to about 2000 cSt, or from about 100 cSt independently to about 1000 cSt in another non-limiting embodiment. The temperature of the hydrocarbon-based fluid sample may range from about 20 C independently to about 250 C, alternatively from about 50 C independently to about 100 C.

In a non-limiting embodiment, the hydrocarbon-based fluid sample may be heated prior to the centrifuging the hydrocarbon-based fluid sample, applying the laser light to the hydrocarbon-based fluid sample, and combinations thereof. Such heating may lower the viscosity of the sample in the absence of a solvent. As used herein with respect to a range, "independently" means that any lower threshold may be used together with any upper threshold to give a suitable alternative range.

The hydrocarbon-based fluid sample may have such a viscosity by itself, or at least one solvent may be added to the hydrocarbon-based fluid sample prior to centrifuging it to adjust the viscosity of the sample. The solvent may have the same solubility parameters as the hydrocarbon-based fluid sample, i.e. only the viscosity parameters of the sample changes and not the solubility parameters. For example, if xylene insoluble foulants within the hydrocarbon-based fluid sample are to be measured, the sample may have its viscosity adjusted by adding toluene to obtain a viscosity within the range mentioned above. In another non-limiting example, to measure asphaltenes, coke, inorganic solids, etc., heptane (or hexane, pentane, or a paraffinic solvent with a solubility parameter in the range of 6.8 to 7.2 cal/cm$^{3^{\wedge}}$1/2) may be added to the hydrocarbon-based fluid sample to obtain a particular viscosity prior to centrifuging. Diluting the hydrocarbon-based fluid sample to a particular viscosity makes the sample more transparent, which gives a clearer measurement of asphaltene stability reserve upon the flocculation point of the asphaltenes.

The solvent may be added to the hydrocarbon-based fluid sample in an effective amount prior to centrifuging the hydrocarbon-based fluid sample to obtain the proper viscosity. The effective amount of the solvent may vary depending on the amount of foulants within the hydrocarbon-based fluid sample. However, to give a general idea, non-limiting examples of the ratio of solvent to hydrocarbon-based fluid range from 20/80 to 40/60 to 50/50.

In another non-limiting embodiment, the solvent having the same solubility as the hydrocarbon-based fluid may be added to the hydrocarbon-based fluid sample in a step-wise fashion, e.g. 0.1 mLs. The solvent may be added to the hydrocarbon-based fluid sample at about the same time as the centrifuging of the hydrocarbon-based fluid sample, before the centrifuging of the hydrocarbon-based fluid sample, after the centrifuging of the hydrocarbon-based fluid sample, and combinations thereof. Once the solvent (e.g. heptane) is in excess with respect to the asphaltene stability, the asphaltenes will precipitate. When the transmittance is measured, an inflection point can be observed in a plot of transmittance vs the volume of added solvent as flocculation begins. The point of inflection, expressed as the asphaltene stability index (ASI) corresponds to the point of asphaltene precipitation and provides a relative measure of the asphaltene's stability in the hydrocarbon-based fluid. An ASI measurement of 0 to 130 may indicate a high fouling potential; a scale of 130-200 may indicate a medium fouling potential; a scale of 200 or higher may indicate a low fouling potential. This procedure is particularly helpful when analyzing crude blends and/or whether to add a chemical additive to enhance dispersion or stability of the foulants within the crude blends. More information related to the asphaltene stability test may be found in the article, "Fine-tune Processing Heavy Crudes in Your Facility", Falkler and Sandu, Hydrocarbon Processing, September 2010, pgs. 67-73.

The laser light may have a wavelength in the near-infrared region, such a wavelength of light ranging from about 800 nm independently to about 2500 nm. Alternatively, the wavelength of light may range from about 1000 nm independently to about 2000 nm, or from about 1300 nm independently to about 1800 nm in another non-limiting embodiment. A detector is used in conjunction with the laser light to measure the transmittance of the sample. Any suitable detector may be used for such a purpose as is known to those skilled in the art of measuring transmittance of hydrocarbon fluids.

In one non-limiting embodiment, the hydrocarbon-based fluid sample may have a continuous dosing of solvent to the sample, while detecting the first transmittance measurement of the centrifuged hydrocarbon-based fluid sample. A second transmittance measurement may be detected of a non-centrifuged hydrocarbon-based fluid sample having the same continuous dosing of solvent to the non-centrifuged hydrocarbon-based fluid sample. The first transmittance measurement may then be compared to the second transmittance measurement to determine the stability of the foulants therein. For comparison purposes, the total amount of solvent and the amount of time for the solvent to be added to the centrifuged sample and the non-centrifuged sample should be about the same.

In another non-limiting embodiment, after measuring at least one transmittance of the centrifuged hydrocarbon-based fluid sample, whether the sample includes a solvent or not, the non-precipitated portion of the hydrocarbon-based fluid sample may be removed from the hydrocarbon-based fluid sample. The solvent may be added to the non-precipitated portion in a step-wise manner, and the non-precipitated portion may be centrifuged, and at least one transmittance measurement may be detected for the non-precipitated portion.

In another non-limiting embodiment, the number or size of flocculated foulant particles may be analyzed by a particle counting technique, such as but not limited to, light scattering, light blocking, ultrasound, videomicroscopy, and combinations thereof. All of the flocculated foulant particles may be detected at one time or at a separate time.

For the light obscuration or light scattering technique, the particles in the hydrocarbon-based fluid sample may pass through a photozone, which is a narrow, rectangular region of uniform light produced by light from a laser. The sample must be sufficiently dilute so the particles may pass one at a time through the illuminated region. As each particle passes through the photozone, the light is either absorbed, refracted, scattered, or combinations thereof depending on the type of sensor or technique used. The illumination and detection system in the sensor is designed to provide a monotonic increase in pulse height with increasing particle diameter.

One non-limiting example of a particle counter is the PAMAS SVSS (small volume syringe system), which is distributed by PAMAS™. A stepper-motor-actuated precision syringe moves the sample through a laser-diode sensor at the optimum flow-rate and an accurate sample volume may be achieved. The PAMAS SVSS is designed for low viscous, aqueous solutions; however, the inventors have discovered that the PAMAS SVSS system may be used with the hydrocarbon-based fluid system. The measuring of transmittance and the counting/sizing the number of flocculated foulant particles may occur at the same time or at different times depending on the types of hydrocarbon fluid measured, the foulants and the machine used to measure the transmittance and the machine used to count/size the flocculated foulant particles.

A Dispersion Technology DT100 ultrasonic particle sizer may be used for ultrasound technologies in one non-limiting example. In another non-limiting embodiment, a Mettler Toledo PVM real time imaging microscope may be used for videomicroscopy techniques.

The hydrocarbon-based fluid within the hydrocarbon-based fluid sample may be or include, but is not limited to, a production fluid, a crude oil, a natural gas condensate, a shale oil, a shale gas condensate, a bitumen, a diluted bitumen (dil-bit), refinery fractions, finished fuel, finished petroleum products, visbreaker bottoms (also known as vistar), heavy fuel oils (e.g. bunker no. 6) and combinations thereof. The amount of the hydrocarbon-based fluid within the hydrocarbon-based fluid sample may range from about 85 vol % independently to about 100 vol %, alternatively from about 90 vol % independently to about 99.9 vol %.

The foulant particles may be or include, but are not limited to, asphaltenes, iron sulfides, waxes, coke, sand, ores, clays, hydrates, naphthenates, and combinations thereof. The diameter of the flocculated foulant particles may range about 0.05 micron or more, alternatively from about 0.1 microns independently to about 100 microns, or from about 1 micron independently to about 10 microns. The foulant particles may be present in the hydrocarbon-based fluid sample in an amount ranging from about 0.01 vol % independently to about 15 vol %, alternatively from about 1 vol % independently to about 10 vol %, or from about 1 vol % independently to about 5 vol %. In another non-limiting embodiment, an amount of foulants may be removed from the hydrocarbon-based fluid sample before or after centrifuging the sample to test the stability of the remaining foulants/sample.

The hydrocarbon-based fluid sample may also include an optional component, such as but not limited to, a dispersant, a foulant inhibitor, an asphaltenes inhibitor, a demulsifier, and combinations thereof. The stability and/or dispersability and/or effectiveness of the optional component may be analyzed by adding the optional component to the hydrocarbon-based fluid sample and using the method to obtain the size and/or number of particles suspended in the hydrocarbon-based fluid sample instead of simply determining the stability of the sample by looking at the amount that precipitates once the component has been added.

Analysis testing of hydrocarbon-based fluid samples with optional components may be used to gauge the efficacy of the optional components to improve foulant stability in hydrocarbon-based fluids. 'Foulant stability' is defined herein to mean that a stable foulant is a foulant that either remains in a dispersed or soluble form within the hydrocarbon-based fluid sample, or the foulant precipitates in a less amount and/or at a slower rate. The foulant inhibitor may increase the foulant stability by causing a higher percentage of the foulant to remain in a dispersed or soluble form or reduces the amount and/or rate of foulant precipitation as compared to an identical fluid sample with the foulant in the absence of the foulant inhibitor. Better differentiation of foulant inhibitor performance may be obtained. Better differentiation of foulant inhibitor performance allows selection and development of better performing products for treating industry production and refining problems.

The invention will be further described with respect to the following Examples, which are not meant to limit the invention, but rather to further illustrate the various embodiments.

EXAMPLES

Example 1

FIG. 1 is a graph illustrating the stability of a hydrocarbon-based fluid sample prior to centrifuging the hydrocarbon-based fluid sample. The normalized power refers to the power (in microwatts) divided by the maximum power at the flocculation peak. The flocculation peak is typically where the hydrocarbon-based fluid sample is the least dark in color and has the maximum transmittance. A transmittance measurement was detected for the hydrocarbon-based fluid sample prior to centrifugation. A hydrocarbon-based fluid sample having a crude oil fluid and measured the asphaltene stability index (ASI) based on a titration plot of the sample. The hydrocarbon-based fluid sample was then centrifuged, and the sample was titrated with 0.1 mLs of heptane in a step-wise fashion, while detecting the transmittance for the centrifuged hydrocarbon-based fluid sample to compare the transmittance measurement of the non-centrifuged sample. The sample was then centrifuged for 5 minutes at 500 rpm.

Figure 2:
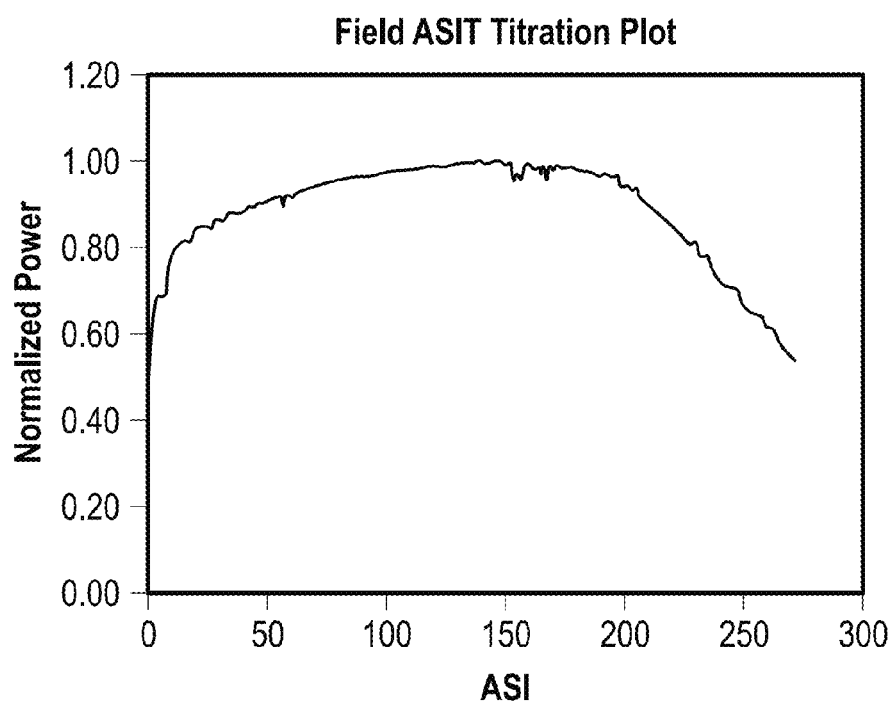
FIG. 2 is a graph illustrating the stability of a hydrocarbon-based fluid sample after centrifuging the hydrocarbon-based fluid sample.

FIG. 2 is a graph illustrating the stability of the hydrocarbon-based fluid sample after centrifuging the hydrocarbon-based fluid sample, which depicts much higher ASI measurements. The hydrocarbon-based fluid sample was centrifuged for 10 minutes at 500 rpm. The hydrocarbon-based fluid sample depicted in FIG. 2 appears to be more stable after being centrifuged.

Example 2

Figure 3:
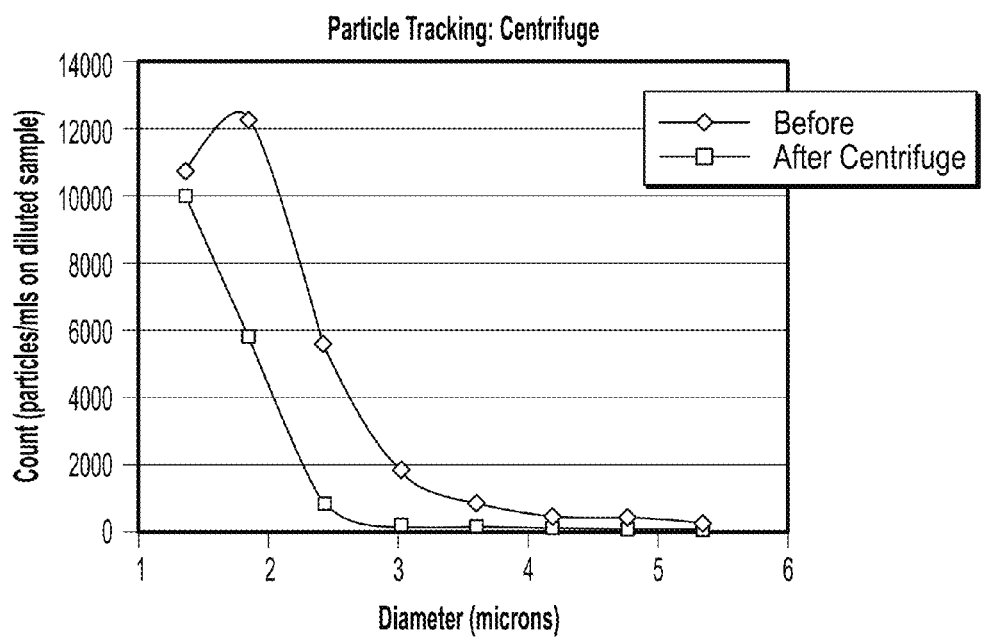
FIG. 3 is a graph illustrating the particle count of the hydrocarbon-based fluid sample before and after centrifuging the hydrocarbon-based fluid sample.

FIG. 3 is a graph illustrating the particle count of the hydrocarbon-based fluid sample before and after centrifuging the hydrocarbon-based fluid sample for 10 minutes at 500 rpm. The hydrocarbon-based fluid sample had a crude oil fluid and measured asphaltenes. The machine used for the particle count was a light obscuration based PAMAS SVSS. As noted by the graph, the particle count before the centrifuging is much higher than the particle count after the centrifuging.

Example 3

Figure 4:
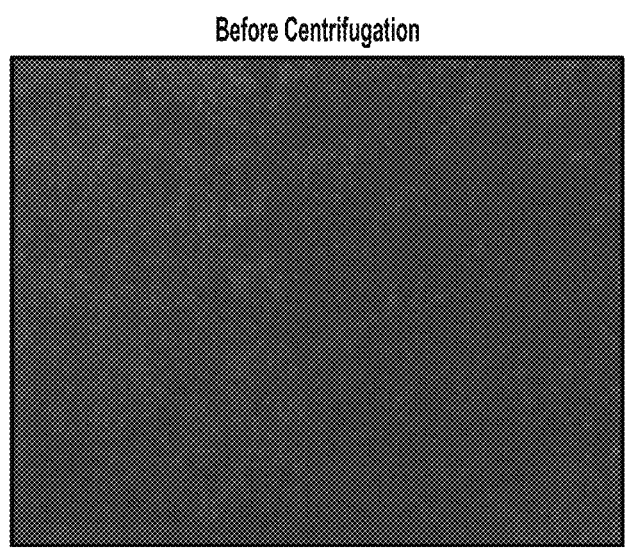
FIG. 4 is a photo taken by videomicroscopy before centrifuging the hydrocarbon-based fluid sample.
Figure 5:
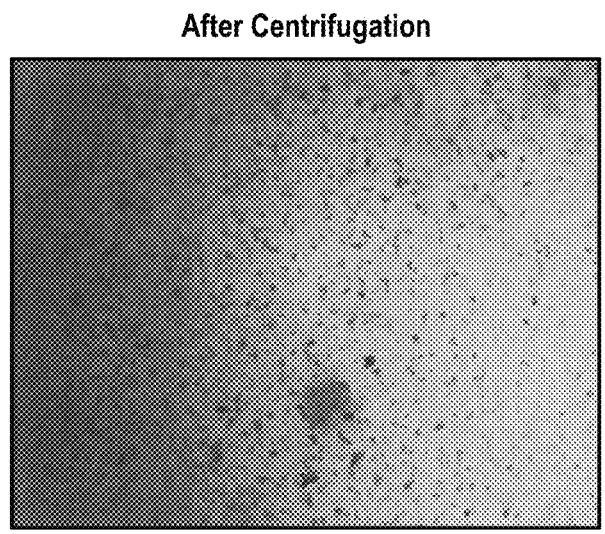
FIG. 5 is a photo taken by videomicroscopy after centrifuging the hydrocarbon-based fluid sample.

FIG. 4 is a photo taken by videomicroscopy before centrifuging a hydrocarbon-based fluid sample, and FIG. 5 is a photo taken by videomicroscopy after centrifuging the same hydrocarbon-based fluid sample for 5 minutes at 500 rpm. The hydrocarbon-based fluid sample had a crude oil fluid and measured asphaltenes. The machine used for the videomicroscopy was an Olympus microscope model BX43. As noted by the comparison of FIG. 5 to FIG. 4, foulant particles are prominently seen in FIG. 5 and software may be used for better image recognition of the foulant particles.

Example 4

Figure 6:
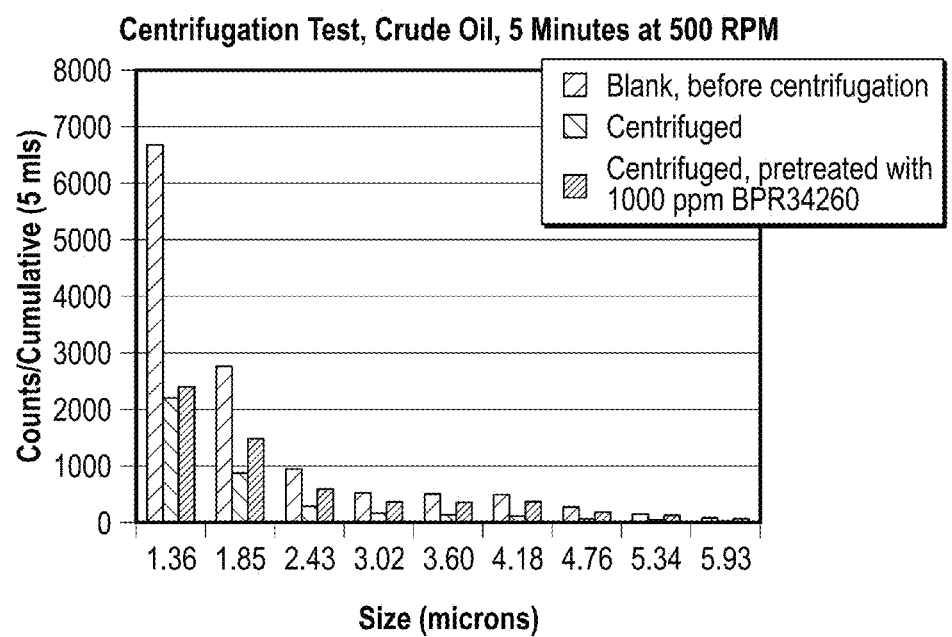
FIG. 6 is a graph illustrating the impact of centrifugation depending on the particle size distribution (PSD) of the foulant particles.

FIG. 6 is a graph illustrating the impact of centrifugation depending on the particle size distribution (PSD) of the foulant particles. The hydrocarbon-based fluid sample was a crude oil fluid and measured asphaltenes. The blank sample represents a sample that has not been centrifuged. The middle bar of each size is a centrifuged sample, and the right bar is a centrifuged sample where 1000 ppm of an asphaltene dispersant from Baker Hughes was added to the sample prior to centrifuging the sample. The centrifuged samples were centrifuged for 5 minutes at 500 rpm. As noted by the graph, the centrifuging had more impact on reducing the foulant count within the sample than adding the dispersant.

Example 5

Figure 7:
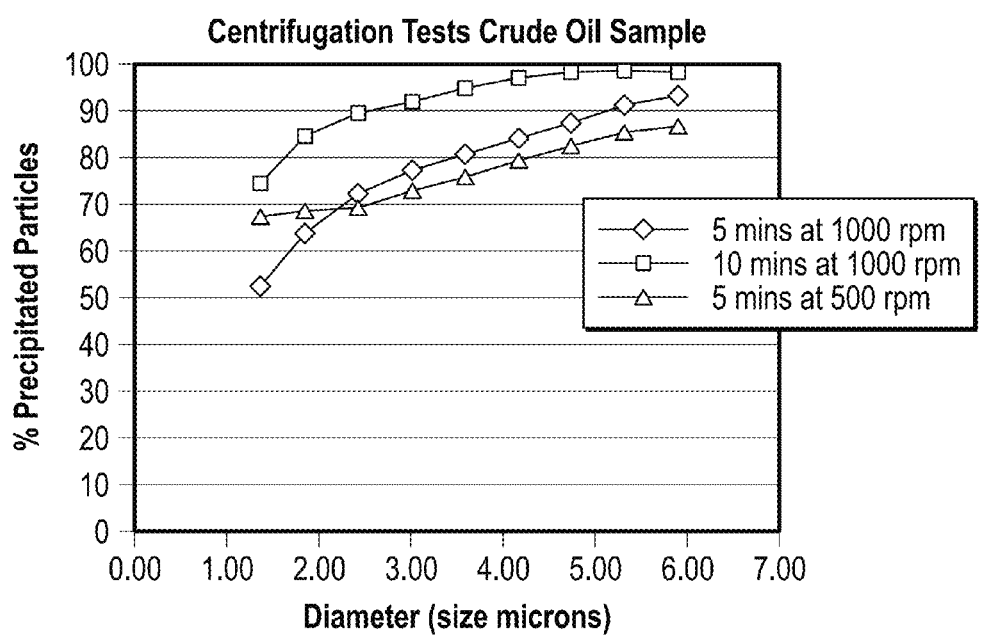
FIG. 7 is a graph illustrating the amount of precipitated particles depending on the size of the particles once centrifuged.

FIG. 7 is a graph illustrating the amount of precipitated particles depending on the size of the particles once centrifuged. The hydrocarbon-based fluid was crude oil and asphaltenes were measured. The sample was centrifuged for 5 minutes at 500 rpm, for 5 minutes at 1000 rpm, and for 10 minutes at 1000 rpm. As noted by the graph, the centrifugation of 10 minutes at 1000 rpm precipitated the most foulants for each size analyzed.

In the foregoing specification, the invention has been described with reference to specific embodiments thereof, and has been described as effective in providing methods for determining the stability of at least one foulant within a hydrocarbon-based fluid sample. However, it will be evident that various modifications and changes can be made thereto without departing from the broader spirit or scope of the invention as set forth in the appended claims. Accordingly, the specification is to be regarded in an illustrative rather than a restrictive sense. For example, specific hydrocarbon-based fluids, solvents, foulant particles, dispersants, foulant inhibitors, and wavelengths of laser light falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, determining a stability of at least one foulant within a hydrocarbon-based fluid sample may be accomplished by a method consisting essentially of or consisting of centrifuging the hydrocarbon-based fluid sample comprising a hydrocarbon-based fluid and foulant particles, wherein the hydrocarbon-based fluid sample has a viscosity ranging from about 0.5 cSt to about 5000 cSt, applying a laser light to the hydrocarbon-based fluid sample where the laser light has a wavelength in the near-infrared region, measuring a first transmittance of the laser light through the hydrocarbon-based fluid sample with a detector, and comparing the first transmittance measurement to a second transmittance measurement of a non-centrifuged hydrocarbon-fluid sample to determine a distribution of foulant particles within the hydrocarbon-based fluid sample.

The words "comprising" and "comprises" as used throughout the claims, are to be interpreted to mean "including but not limited to" and "includes but not limited to", respectively.

What is claimed is:

1. A method to determine a stability of at least one foulant within a hydrocarbon-based fluid sample comprising:
   centrifuging a hydrocarbon-based fluid sample comprising a hydrocarbon-based fluid and foulant particles, wherein the hydrocarbon-based fluid sample has a viscosity ranging from about 0.5 cSt to about 5000 cSt;
   applying a laser light to the hydrocarbon-based fluid sample, wherein the laser light has a wavelength in the near-infrared region ranging from about 800 nm independently to about 2000 nm;
   measuring a first transmittance of the laser light through the hydrocarbon-based fluid sample with a detector; and
   comparing the first transmittance measurement to a second transmittance measurement of a non-centrifuged hydrocarbon-fluid sample to determine a distribution of foulant particles within the hydrocarbon-based fluid sample.

2. The method of claim 1, further comprising analyzing the number or size of flocculated foulant particles by a technique selected from the group consisting of light scattering, light blocking, ultrasound, videomicroscopy, and combinations thereof.

3. The method of claim 2, wherein the measuring the first transmittance and analyzing the number of flocculated foulant particles occur at the same time or at different times.

4. The method of claim 1, further comprising adding at least one solvent to the hydrocarbon-based fluid sample at a time selected from the group consisting of about the same time as the centrifuging, before the centrifuging, after the centrifuging, and combinations thereof.

5. The method of claim 4, wherein the adding at least one solvent occurs in a step-wise manner, and wherein the total amount of the at least one solvent within the hydrocarbon-based fluid sample ranges from about 20 vol % to about 80 vol %.

6. The method of claim 5, wherein the at least one solvent is selected from the group consisting of heptane, toluene, hexane, pentane, xylene, a paraffinic solvent having a solubility range of about 6.8 to 7.2 $(cal/cm3)^{1/2}$, and combinations thereof.

7. The method of claim 1, wherein the amount of the hydrocarbon-based fluid within the hydrocarbon-based fluid sample ranges from about 20 vol % to about 100 vol %.

8. The method of claim 1, wherein the sizes of the flocculated foulant particles are about 0.05 micron or more.

9. The method of claim 1, wherein the centrifuging occurs for at least 30 seconds.

10. The method of claim 1, further comprising adding at least one solvent to the hydrocarbon-based fluid prior to centrifuging the hydrocarbon-based fluid sample.

11. The method of claim 1, wherein the foulant particles are present in the hydrocarbon-based fluid sample in an amount ranging from about 0.01 vol % to about 10 vol %.

12. The method of claim 1, wherein the hydrocarbon-based fluid sample further comprises a component selected from the group consisting of a dispersant, a foulant inhibitor, and combinations thereof.

13. The method of claim 1, further comprising heating the hydrocarbon-based fluid sample prior to the method procedure selected from the group consisting of centrifuging, applying the laser light, and combinations thereof.

14. The method of claim 1, wherein the hydrocarbon-based fluid is selected from the group consisting of a production fluid, crude oil, natural gas condensate, shale oil, shale gas condensate, bitumen, diluted bitumen (dil-bit), refinery fractions, finished fuel, finished petroleum products, and combinations thereof.

15. The method of claim 1, wherein the foulant particles are selected from the group consisting of asphaltenes, iron sulfides, waxes, coke, sand, ores, clays, hydrates, naphthenates, and combinations thereof.

16. A method to determine a stability of at least one foulant within a hydrocarbon-based fluid sample comprising:
   centrifuging a hydrocarbon-based fluid sample comprising a hydrocarbon-based fluid and foulant particles in an amount ranging from about 0.01 vol % to about 10 vol %, wherein the hydrocarbon-based fluid sample has a viscosity ranging from about 0.5 cSt to about 5000 cSt;
   adding at least one solvent to the hydrocarbon-based fluid sample at a time selected from the group consisting of about the same time as the centrifuging, before the centrifuging, after the centrifuging, and combinations thereof;
   applying a laser light to the hydrocarbon-based fluid sample, wherein the laser light has a wavelength in the near-infrared region ranging from about 800 nm to about 2000 nm;
   measuring at least one transmittance of the laser light through the hydrocarbon-based fluid sample with a detector;
   comparing the at least one transmittance measurement to a second transmittance measurement of the laser light through a non-centrifuged hydrocarbon-based fluid sample having the effective amount of the at least one solvent at the time of foulant flocculation; and
   analyzing the number or size of flocculated foulant particles by a technique selected from the group consisting of light scattering, light blocking, ultrasound, videomicroscopy, and combinations thereof.

17. A method to determine a stability of at least one foulant within a hydrocarbon-based fluid sample comprising in any order:
   centrifuging a hydrocarbon-based fluid sample for at least 30 seconds where the hydrocarbon-based fluid sample comprises a hydrocarbon-based fluid and foulant particles selected from the group consisting of asphaltenes, iron sulfides, waxes, coke, sand, ores, clays, hydrates, naphthenates, and combinations thereof;

adding an effective amount of at least one solvent to flocculate at least a portion of the foulant particles;

applying a laser light to the hydrocarbon-based fluid sample, wherein the laser light has a wavelength in the near-infrared region ranging from about 800 nm independently to about 2000 nm;

measuring at least one transmittance of the laser light through the hydrocarbon-based fluid sample with a detector;

comparing the at least one transmittance measurement to a second transmittance measurement of the laser light through a non-centrifuged hydrocarbon-based fluid sample having the effective amount of the at least one solvent at the time of foulant flocculation; and analyzing the number or size of flocculated foulant particles by a technique selected from the group consisting of light scattering, light blocking, ultrasound, videomicroscopy, and combinations thereof.

\* \* \* \* \*